US008961849B2

(12) United States Patent
Hayes et al.

(10) Patent No.: US 8,961,849 B2
(45) Date of Patent: *Feb. 24, 2015

(54) NON-COMPLIANT MEDICAL BALLOON HAVING AN INTEGRAL WOVEN FABRIC LAYER

(71) Applicant: Bard Peripheral Vascular, Inc., Tempe, AZ (US)

(72) Inventors: Kelli Hayes, Athens, TX (US); Lanny R. Pepper, Larue, TX (US); William F. Davies, Jr., Athens, TX (US)

(73) Assignee: Bard Peripheral Vascular, Inc., Tempe, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/690,477

(22) Filed: Nov. 30, 2012

(65) Prior Publication Data
US 2013/0085445 A1 Apr. 4, 2013

Related U.S. Application Data

(63) Continuation of application No. 13/206,739, filed on Aug. 10, 2011, now Pat. No. 8,323,546, which is a continuation of application No. 11/751,326, filed on May 21, 2007, now Pat. No. 8,002,741, which is a continuation of application No. 10/966,970, filed on Oct. 15, 2004, now Pat. No. 7,309,324.

(51) Int. Cl.
B29D 29/10 (2006.01)
A61M 29/00 (2006.01)
A61M 25/10 (2013.01)
B32B 37/12 (2006.01)

(52) U.S. Cl.
CPC .............. *A61M 25/10* (2013.01); *A61M 25/104* (2013.01); *A61M 2025/1075* (2013.01); *A61M 25/1029* (2013.01); *B32B 37/1284* (2013.01)
USPC ....................................... 264/231; 604/96.01

(58) Field of Classification Search
CPC .............. A61M 25/104; A61M 25/10; A61M 25/1002; A61M 25/1029; A61M 2025/1075; A61M 25/1027; A61M 25/005; A61M 25/0045; A61F 2/958
USPC ........................... 604/508, 509, 95.04, 96.01, 604/103.06–103.09, 103.13, 103.12; 264/231
See application file for complete search history.

(56) References Cited

U.S. PATENT DOCUMENTS 4,637,396 A * 1/1987 Cook .............................. 606/194
6,746,425 B1 * 6/2004 Beckham ................. 604/103.09
7,309,324 B2 * 12/2007 Hayes et al. ............... 604/96.01

* cited by examiner

Primary Examiner — Manuel Mendez
(74) Attorney, Agent, or Firm — King & Schickli, PLLC

(57) ABSTRACT

A non-compliant medical balloon may be changed from a deflated state to an inflated state by increasing pressure within the balloon. The non-compliant medical balloon is composed of a woven fabric layer composed of at least two woven fabric fibers forming an angle. The angle remains substantially unchanged when the balloon changes from a deflated state to an inflated state.

21 Claims, 14 Drawing Sheets

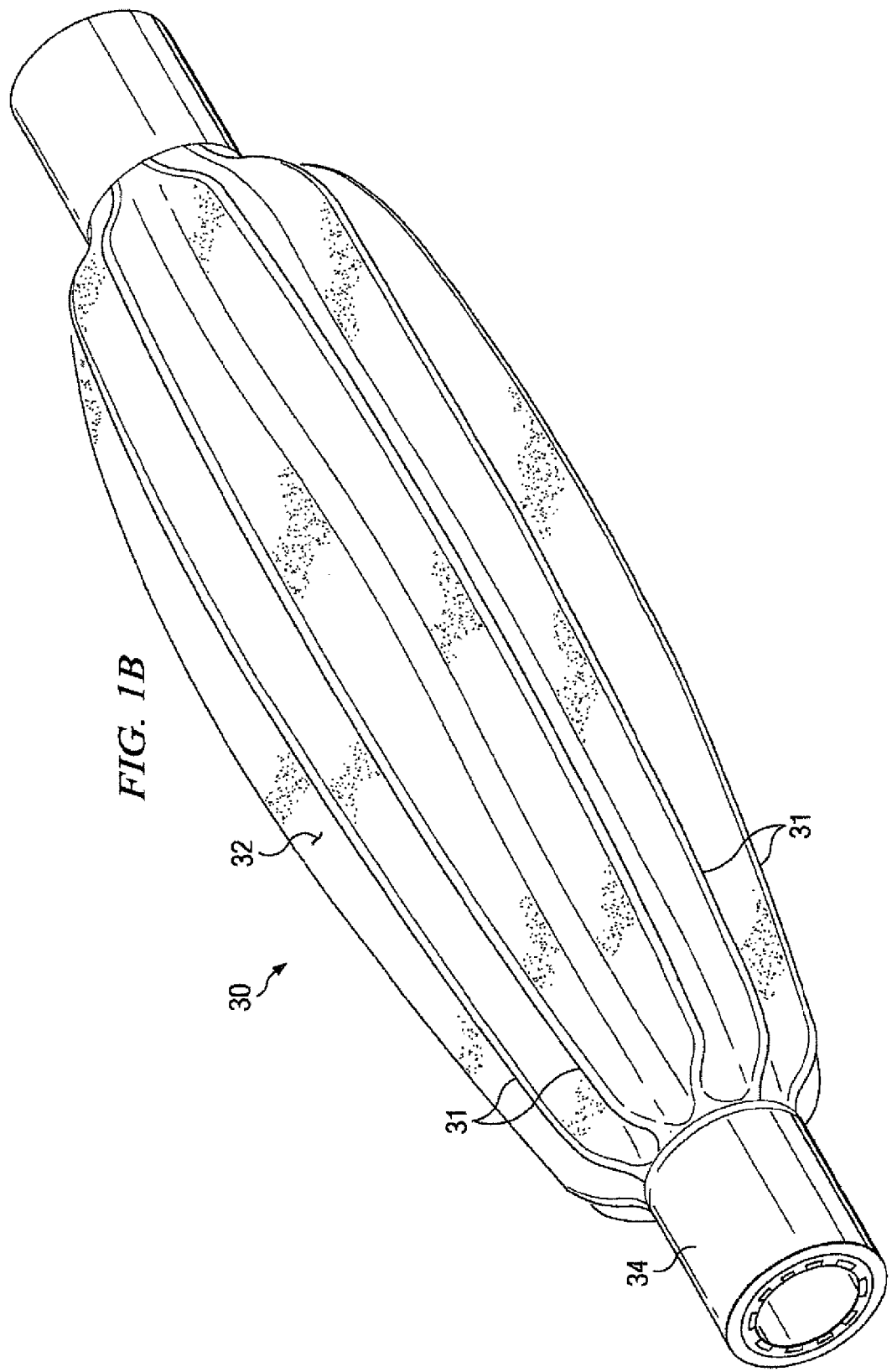

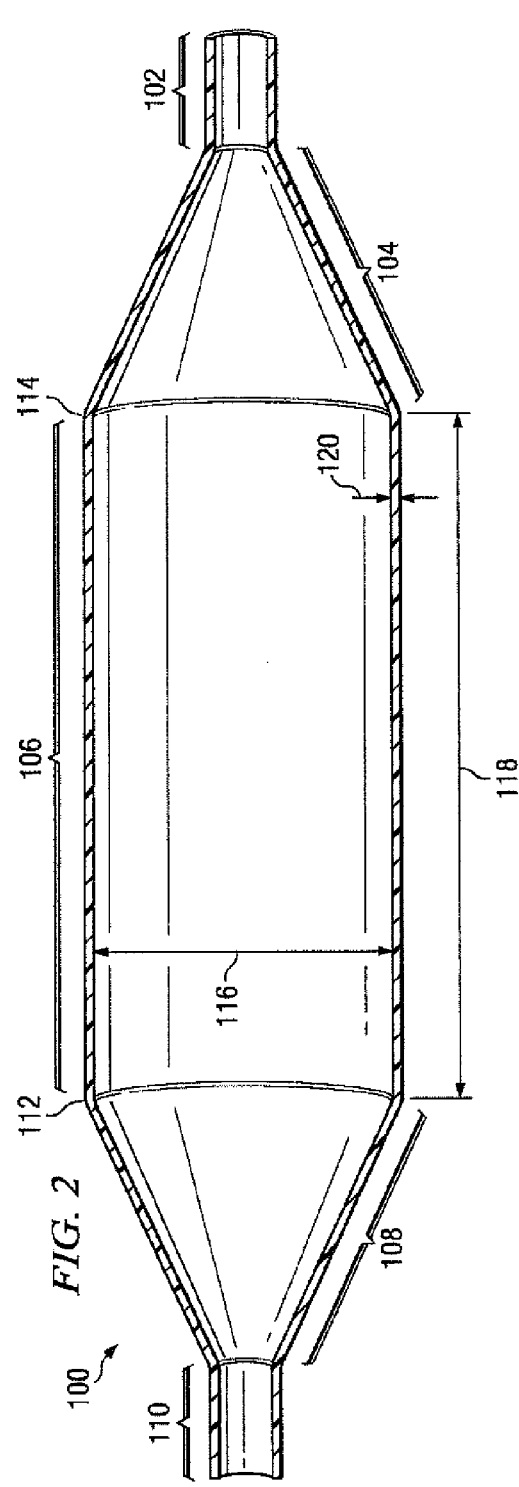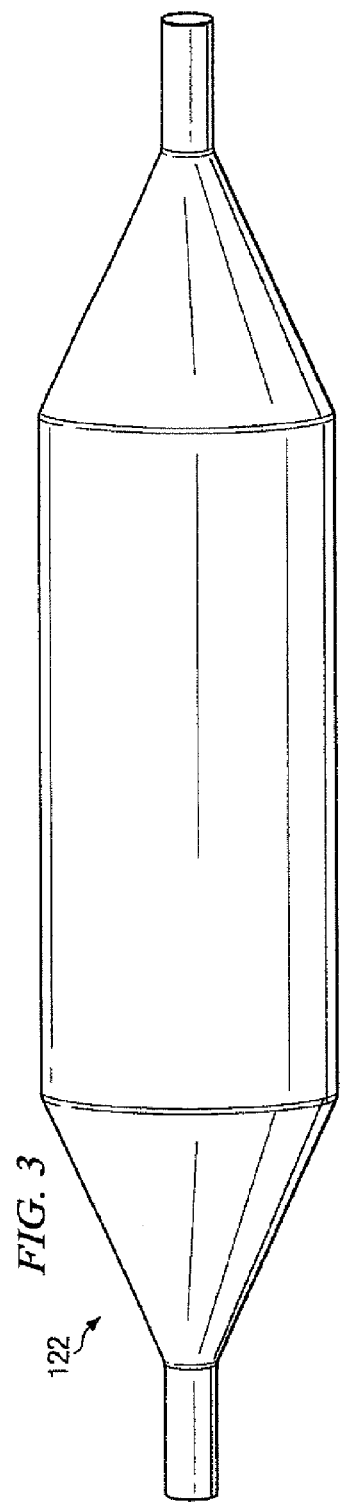

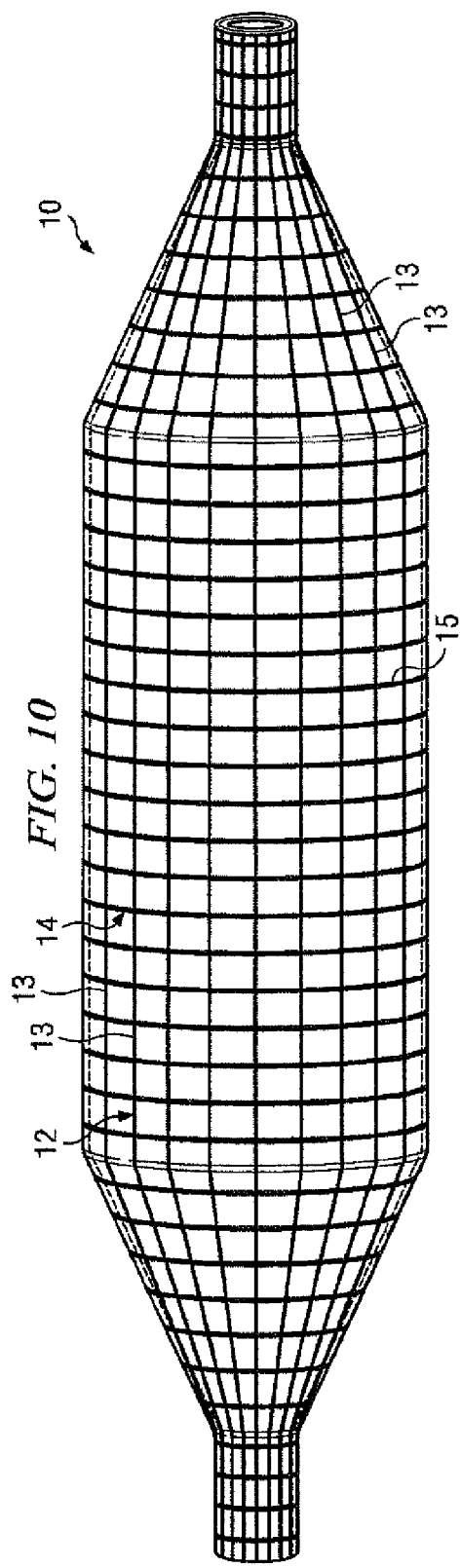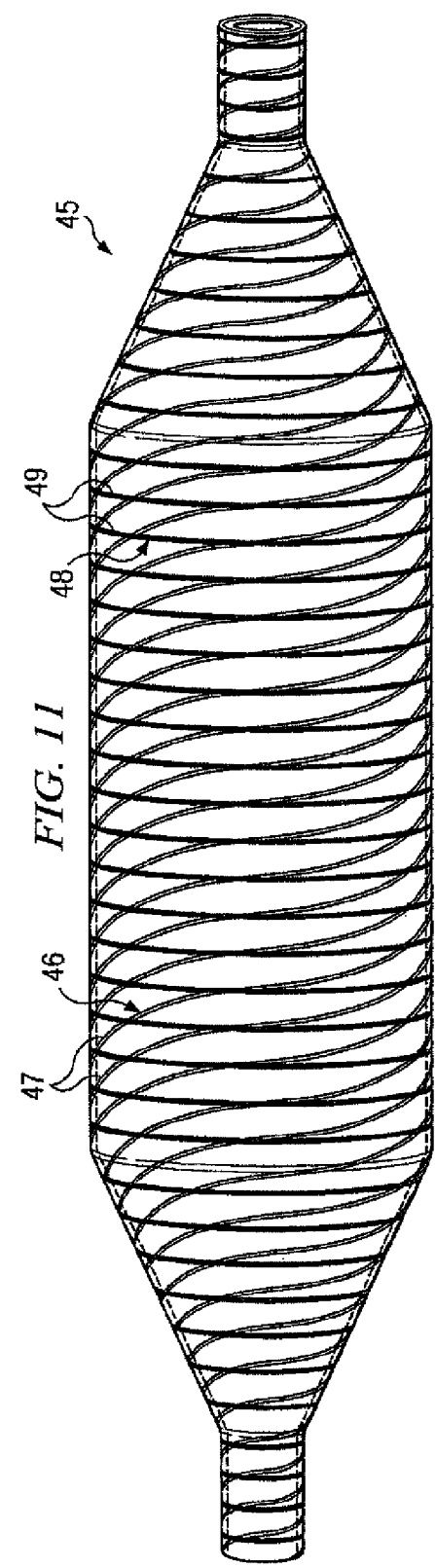

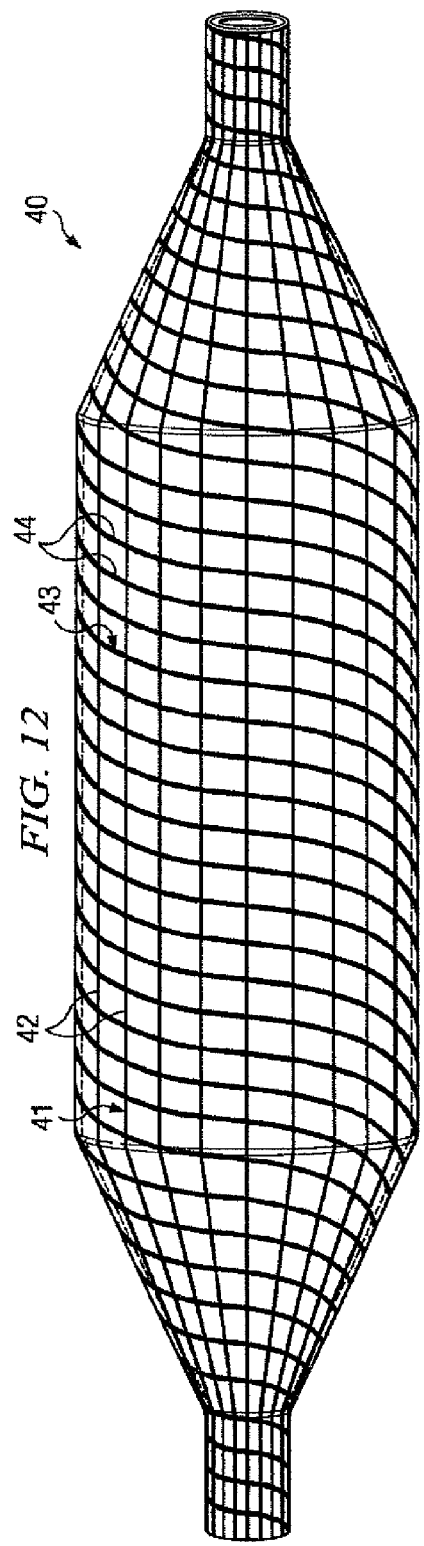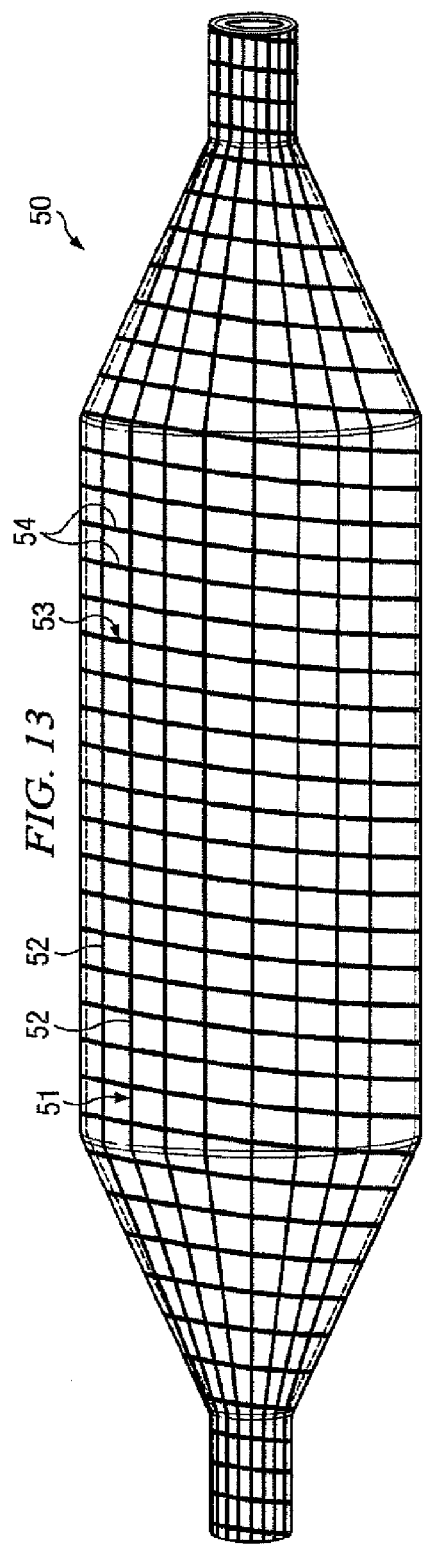

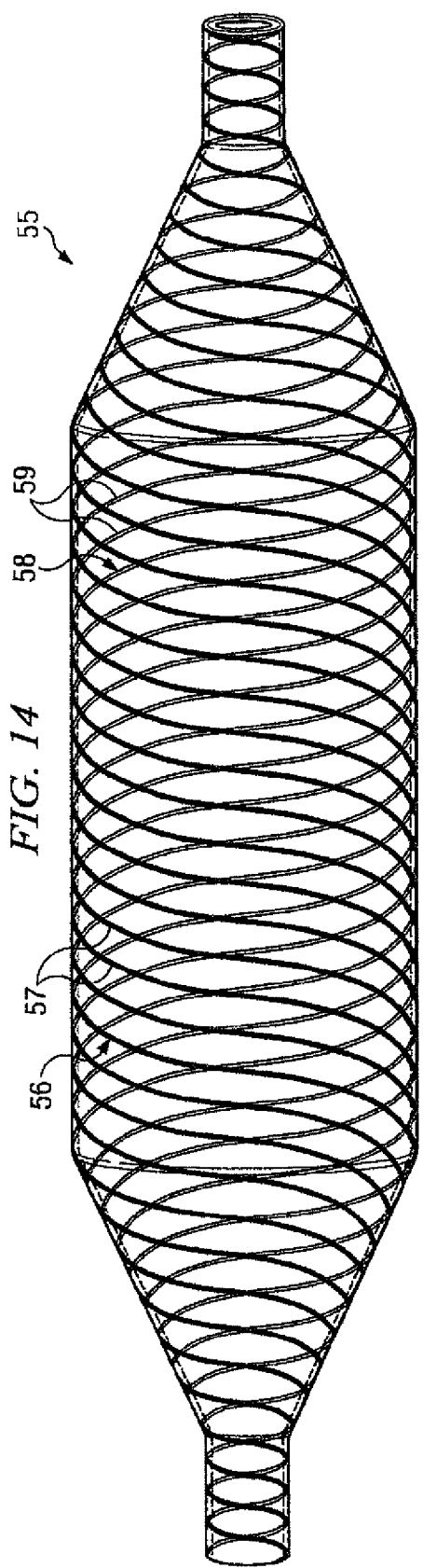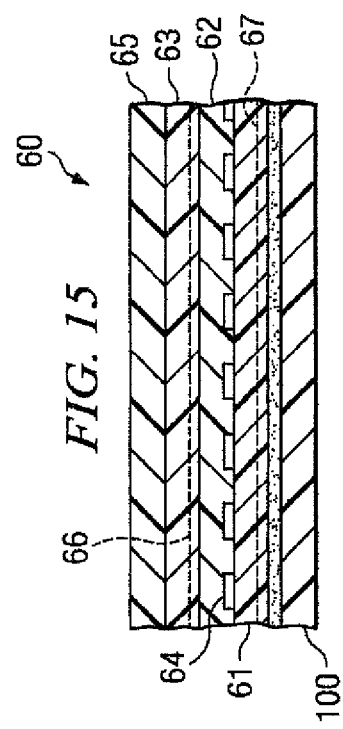

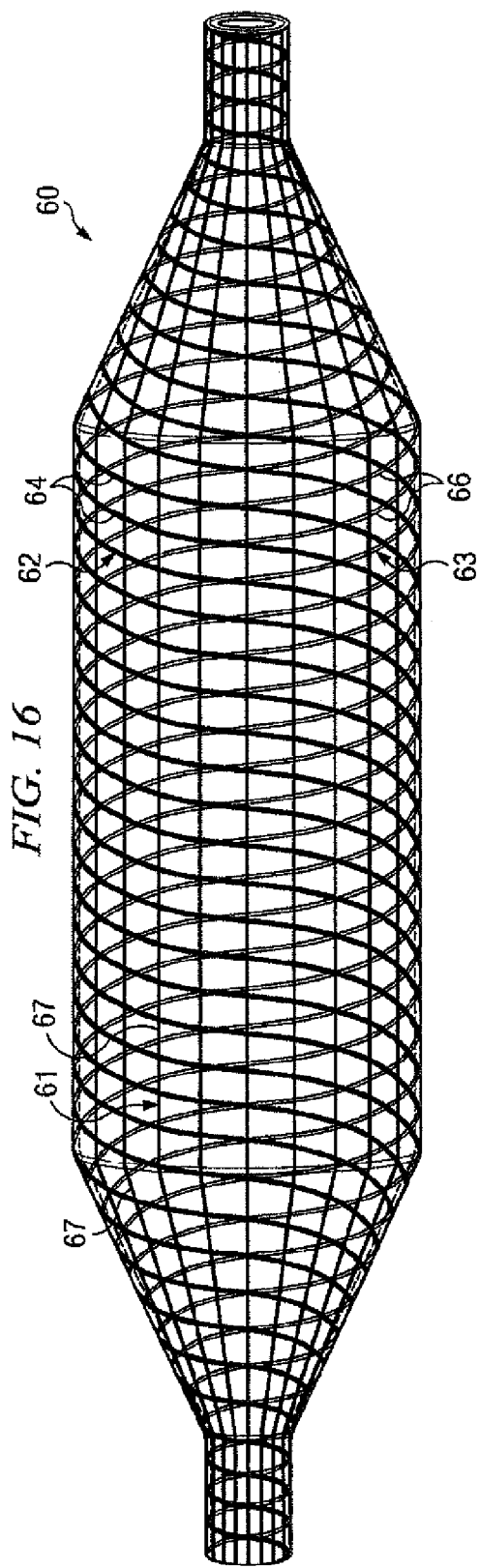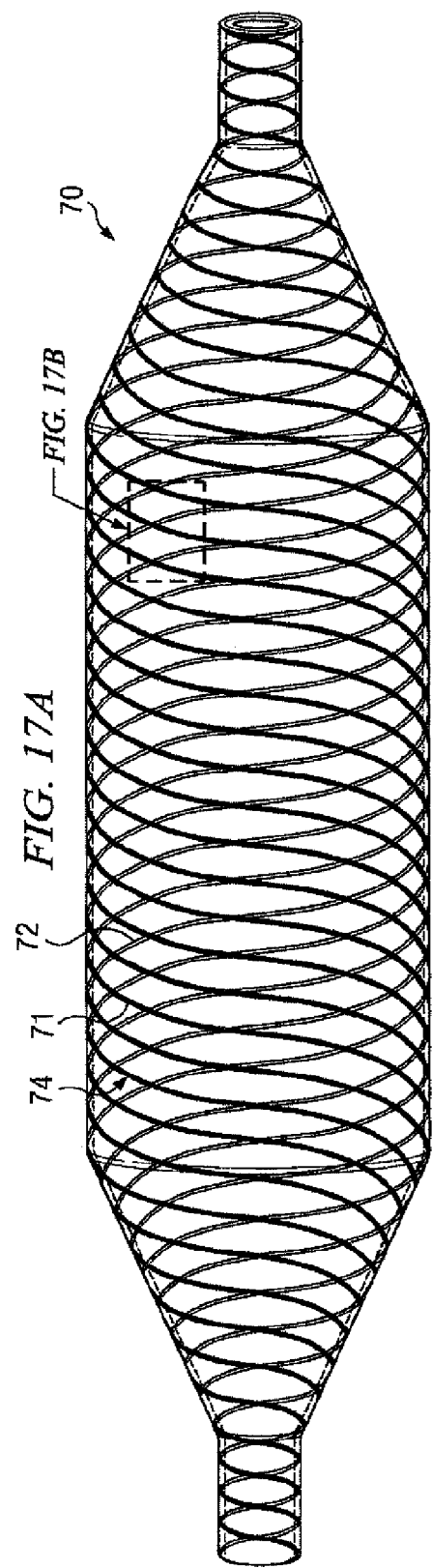

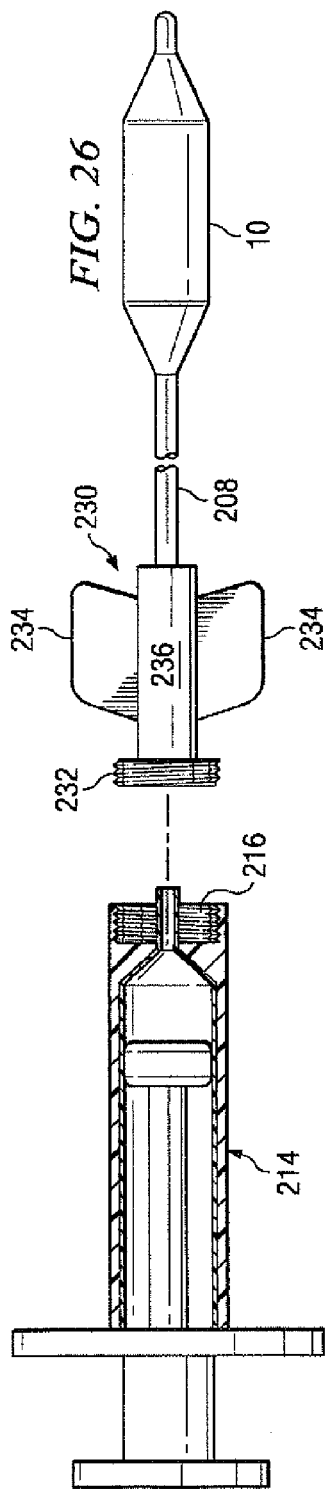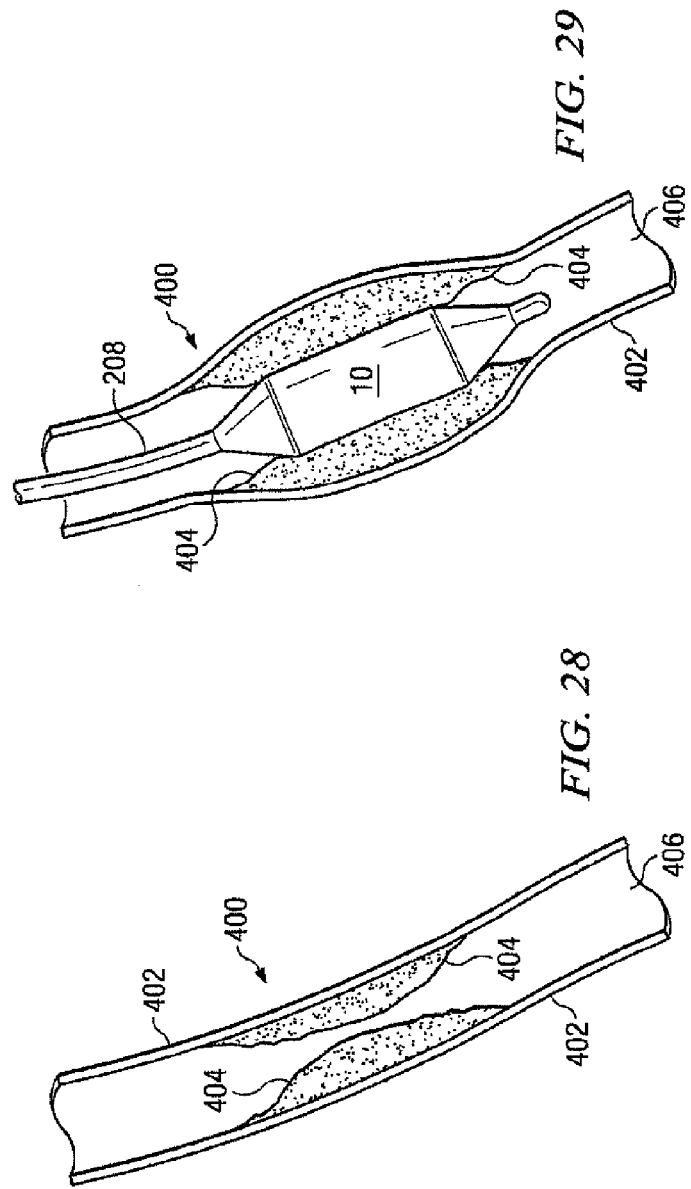
FIG. 26
FIG. 28
FIG. 29

NON-COMPLIANT MEDICAL BALLOON HAVING AN INTEGRAL WOVEN FABRIC LAYER

CROSS REFERENCE TO RELATED APPLICATIONS

This application is a continuation of U.S. application Ser. No. 13/206,739, titled NON-COMPLIANT MEDICAL BALLOON HAVING AN INTEGRAL WOVEN FABRIC LAYER, filed Aug. 10, 2011, which is a continuation of U.S. application Ser. No. 11/751,326, titled NON-COMPLIANT MEDICAL BALLOON HAVING AN INTEGRAL WOVEN FABRIC LAYER, filed May 21, 2007, which is a continuation of U.S. application Ser. No. 10/966,970, entitled NON-COMPLIANT MEDICAL BALLOON HAVING AN INTEGRAL WOVEN FABRIC LAYER, filed Oct. 15, 2004 , the specification of which are incorporated herein by reference.

TECHNICAL FIELD OF THE INVENTION

This invention is related to medical balloons, in particular non-compliant medical balloons used with a balloon catheter in medical procedures such as angioplasty.

BACKGROUND OF THE INVENTION

Medical balloons have been widely used in medical procedures. Typically, an uninflated medical balloon is inserted into a body-space. When the medical balloon is inflated, the volume of the medical balloon expands, and the body-space is similarly expanded. In procedures such as angioplasty, the medical balloon may be used to open a collapsed or blocked artery.

Generally, medical balloons have been made of rubber or other compliant substances. To inflate the compliant medical balloons, pressure is increased within the medical balloon, causing the compliant substance to stretch. As more and more pressure is applied to the inner surface of the medical balloon, the medical balloon expands larger and larger until the medical balloon bursts. A typical medical balloon will burst at approximately 7-20 atmospheres or about 100-300 psi.

One of the principal difficulties in the use of medical balloons in medical procedures is controlling the dimensions of the inflated medical balloon. The pressure introduced must be sufficient to inflate the medical balloon to the proper size, however too much pressure may overinflate the balloon. Overinflating a medical balloon may cause the balloon to expand to a size that may cause stress on the body and may even damage the body. In the worst case, the excess of pressure may burst the balloon, which can lead to serious complications.

While medical balloons are typically made to close tolerances so that the inflation pressure of the balloon is predictable, variations in the materials used may cause compliant medical balloons to either under-inflate or overinflate for a given pressure. The equipment used to inflate and control the pressure of the balloon must be carefully calibrated and sufficiently accurate to deliver the expected pressure with minimal deviations.

Medical balloons are commonly used in angioplasty, orthopaedics and other medical procedures where it is necessary to force a space within the body.

Non-compliance, or the ability not to expand beyond a predetermined size on pressure and to maintain substantially a profile, is a desired characteristic for balloons. A non-compliant medical balloon is less likely to rupture or dissect the vessel as the balloon expands. The burst pressure of a balloon is the average pressure required to rupture a balloon; usually measured at body temperature.

Further difficulties often arise in guiding a balloon catheter into a desired location in a patient due to the friction between the apparatus and the vessel through which the apparatus passes. The result of this friction may be failure of the balloon due to abrasion and puncture during handling and use. Failure may also result from over-inflation.

Therefore, what is needed is a non-compliant medical balloon that can be inflated with pressure such that the balloon maintains its inflated dimensions without further expanding when additional pressure is applied.

SUMMARY OF THE INVENTION

A non-compliant medical balloon may be changed from a deflated state to an inflated state by increasing pressure within the balloon. The non-compliant medical balloon is composed of a woven fabric layer composed of at least two woven fabric fibers forming an angle. The angle remains substantially unchanged when the balloon changes from a deflated state to an inflated state.

BRIEF DESCRIPTION OF THE DRAWINGS

FIG. 1B illustrates a deflated fiber-reinforced medical BALLON;

FIG. 2 illustrates an inflated balloon base layer;

FIG. 3 illustrates a balloon-shaped mandrel;

FIG. 10 illustrates a fiber-reinforced medical balloon with a longitudinal first fiber layer and a circumferential second fiber layer;

FIG. 11 illustrates a fiber-reinforced medical balloon with a longitudinal first fiber layer and an angled second fiber layer;

FIG. 12 illustrates a fiber-reinforced medical balloon having an angled first fiber layer and a circumferential second fiber layer;

FIG. 13 illustrates a fiber-reinforced medical balloon having a longitudinal first fiber layer and an angled second fiber layer;

FIG. 14 illustrates a fiber-reinforced medical balloon having an angled first fiber layer and an angled second fiber layer;

FIG. 15 illustrates a cross-section of a balloon base layer, an adhesive layer, a first fiber layer, a second fiber layer, a third fiber layer and an outer coating layer;

FIG. 16 illustrates a fiber-reinforced medical balloon having a longitudinal first fiber layer, an angled second fiber layer and a third fiber layer;

FIG. 17A illustrates a fiber-reinforced medical balloon having a woven fiber layer;

FIG. 26 illustrates a balloon catheter, connector and syringe;

FIG. 28 illustrates a cross-section of a blocked vessel;

FIG. 29 illustrates a cross-section of a blocked vessel containing an inflated balloon catheter;

DETAILED DESCRIPTION OF THE INVENTION

Figure 1A:
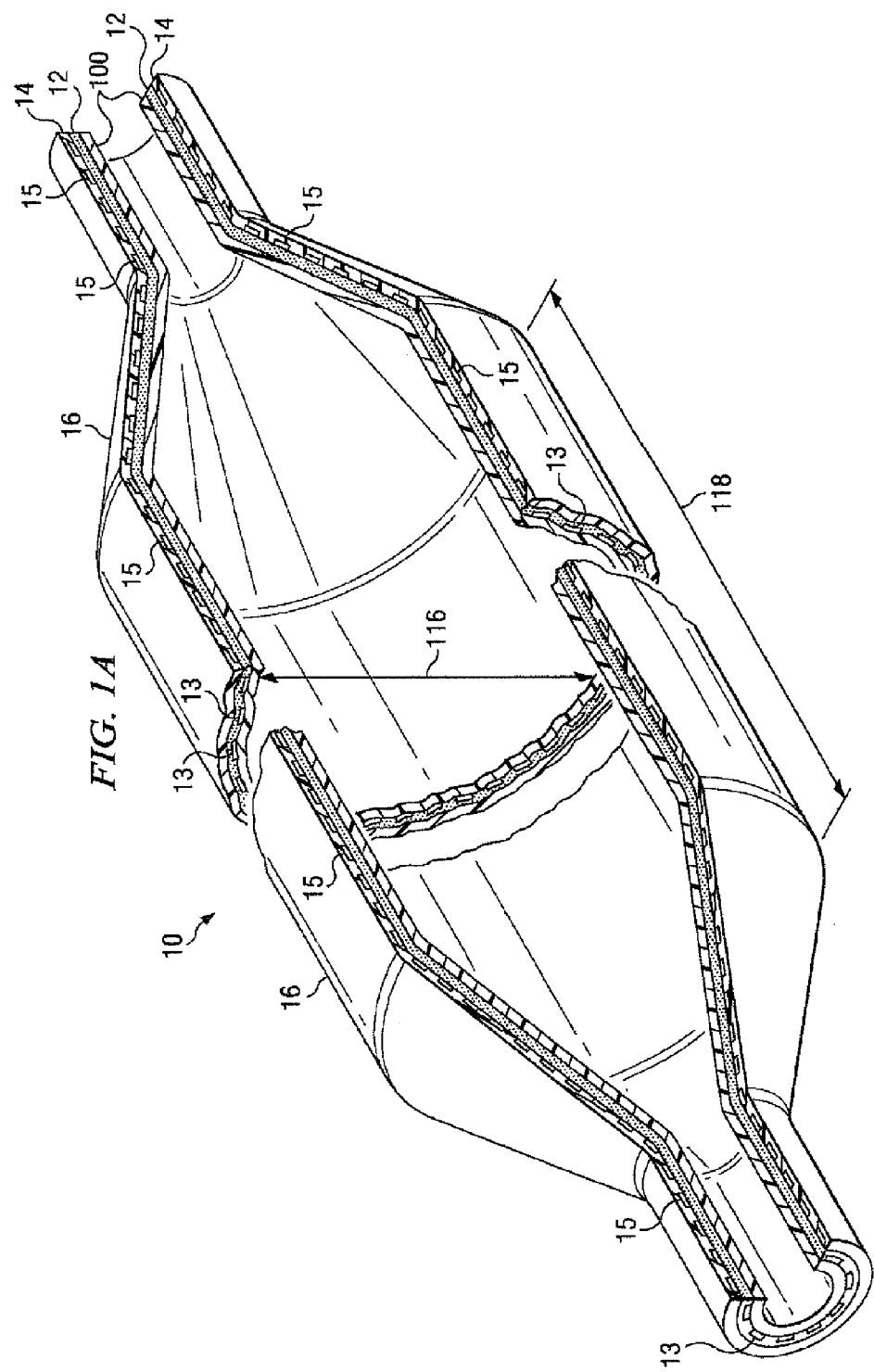
FIG. 1A illustrates a semi-cross section of a fiber-reinforced medical balloon.

Referring now to the drawings, wherein like reference numbers are used to designate like elements throughout the various views, several embodiments of the present invention are further described. The FIGURES are not necessarily drawn to scale, and in some instances the drawings have been exaggerated or simplified for illustrative purposes only. One of ordinary skill in the art will appreciate the many possible applications and variations of the present invention based on the following examples of possible embodiments of the present invention.

With reference to FIG. 1A, a cross section of an inflated fiber-reinforced medical balloon 10 is shown. With reference to FIG. 1B, a cross section of a deflated fiber-reinforced medical balloon 30, is shown. The fiber-reinforced balloon, 10 and 30, is substantially non-compliant, having limited expansion characteristics. As pressure is applied to the interior of a deflated balloon 30 through catheter inlet connector 34, the deflated balloon 30 inflates. Balloon folds 31 in outer surface 32 decrease the diameter of the medical balloon 30 for insertion. As the deflated medical balloon 30 inflates, the balloon folds 31 substantially disappear until the balloon 30 reaches an inflated size, as indicated by balloon 10 in FIG. 1A. Because the medical balloon 10 is non-compliant, once the balloon 10 is fully inflated, it has a length 118 and diameter 116 that do not change as the pressure on the interior of the balloon 10 increases.

The diameter 116 of an inflated fiber-reinforced medical balloon 10 in accordance with the one embodiment may be about ten millimeters. Balloons 10 with a diameter 116 of about five millimeters to twenty millimeters have been developed. The length 118 of an inflated fiber-reinforced medical balloon 10 in accordance with one embodiment may be about eight centimeters. Balloons 10 with a length 118 of two centimeters, three centimeters, four centimeters, six centimeters and eight centimeters have been made. The inclination angle of the cone portion 108 of an inflated fiber-reinforced medical balloon 10 in accordance with the disclosed embodiment may be about twenty degrees. It will be recognized by those having skill in the art that the fiber-reinforced balloon 10 could be made in a wide variety of diameters 116 and lengths 118 and with a variety of inclinations at the cone portion 108 of the balloon.

The fiber-reinforced balloon 10 is generally suitable for use as a medical balloon. Medical balloons are commonly used in angioplasty, orthopaedics and other medical procedures where it is necessary to create a space within the body. It may be recognized by those skilled in the art that the qualities of a fiber-reinforced balloon 10 may make the balloon 10 suitable for other uses. The fiber-reinforced balloons 10 may be used non-medically to create space or otherwise. The fiber-reinforced balloons 10 may be used in ways beyond the present uses of medical balloons.

The fiber-reinforced medical balloon 10 may integrally include base balloon layer 100, a first layer of thin inelastic fibers 12 made up of one or more fibers 13. The fiber-reinforced medical balloon 10 may integrally include a second layer of thin inelastic fibers 14 made up of one or more fibers 15. An outer coating layer 16 may be integrally included in the fiber-reinforced medical balloon 10.

Each fiber 13 is typically fixed relative to other fibers in the first fiber layer 12 and other fibers in the balloon 10. The thin inelastic fibers 13 of the first fiber layer 12 may be characterized by a high tensile strength. As required for medical uses, the fiber-reinforced balloons 10 provide superior burst strength. The fiber-reinforced balloon 10 may also resist abrasion, cuts and punctures. It may be recognized that enhanced structural integrity may result from the fiber reinforcement.

With reference to FIG. 2, a fiber reinforced medical balloon may include a base layer 100. The base layer 100 may be in the shape of a standard medical balloon, ore any other suitable shape. A standard polymeric balloon may function as a base layer 100 for the fiber-reinforced medical balloon 10. The base balloon layer 100 typically includes a first passage region 102 which may be formed as a narrow cylinder fashioned to attach to the tube of a catheter. A second passage region 110 may be similarly formed as a narrow tube. The first passage region 102 is formed adjacent to a first cone region 104. The first cone region 104 expands the diameter of the first passage region to meet the barrel region 106, marked by a first edge 114. The first cone region 104 is typically constructed at an angle of about twelve to twenty degrees.

The barrel region 106 is characterized by a length 118 and a diameter 116. The barrel region 106 meets the second cone region 108 at a second edge 112. The second cone 108 meets the second passage region 110.

The base layer balloon 100 is typically formed of a thin film polymeric material, or other suitable materials with high strength relative to film thickness. Polymers and copolymers that can be used for the base balloon 100 include the conventional polymers and copolymers used in medical balloon construction, such as, but not limited to, polyethylene, (PET), polycaprolactam, polyesters, polyethers, polyamides, polyurethanes, polyimides, ABS, nylons, copolymers, polyester/polyether block copolymers, ionomer resins, liquid crystal polymers, and rigid rod polymers. The base layer balloon 100 may typically be formed as a blow-molded balloon of highly oriented polyethylene terephthalate (PET).

The strength of the fiber-reinforced balloons 10 permits the use of base layer balloons 100 having a wall thickness 120 less than conventional or prior art balloons without sacrifice of burst strength, abrasion resistence, or puncture resistance. In accordance with the disclosed embodiment, the base layer balloon 100 may have a wall thickness 120 of 0.0008 inch. It will be recognized by those skilled in the art that the wall thickness 120 of the base layer balloon 100 may be diminished as required. Because it is possible for a fiber-reinforced balloon 10 to omit the PET balloon base layer 100, the balloon wall thickness 120 can be selected to be arbitrarily small.

The balloon base layer 100 may be omitted from a fiber-reinforced balloon 10, in accordance with one embodiment. The base layer of a polymer 100, which has been cured into the shape of a balloon may be formed. This polymer base layer 100 forms the inner polymeric wall of the fiber reinforced balloon. With reference to FIG. 3, a removable mandrel 122 may be used as a base for application of the polymer. After the polymer is cured, the mandrel 122 may be removed by standard means such as an application of heat to destructure the mandrel 122.

A removable base balloon may be used as the mandrel 122. The mandrel 122 may be made from a variety of materials. The mandrel 122 may be made in the shape of the interior wall of the desired finished balloon. The mandrel 122 may be made of collapsible metal or polymeric bladder, foams, waxes, low-melting metal alloys, and the like. Once the composite balloon is developed and laminated, the base balloon or mandrel 122 may be removed by melting, dissolving, fracturing, compressing, pressurizing or other suitable removal techniques.

In using the mandrel 122 arrangement, alternative processing techniques can be employed which do not limit the parameters of temperature, force, pressure, etc., during the lamentation process. The materials used for the balloon construction are not limited to those which conform to the present art of forming a balloon with pressure, temperature and force, such as, for example, those utilized for forming a balloon from a tube made from a polymeric material. Stronger fiber-reinforced balloons 10, with higher pressure and better damage resistance, can be formed with smaller geometries, in particular balloons having thinner walls. The resulting fiber-reinforced balloons 10 can be stronger, softer and more flexible. This minimizes the necessary introducer passage while providing higher performance at higher pressures.

Figure 4:
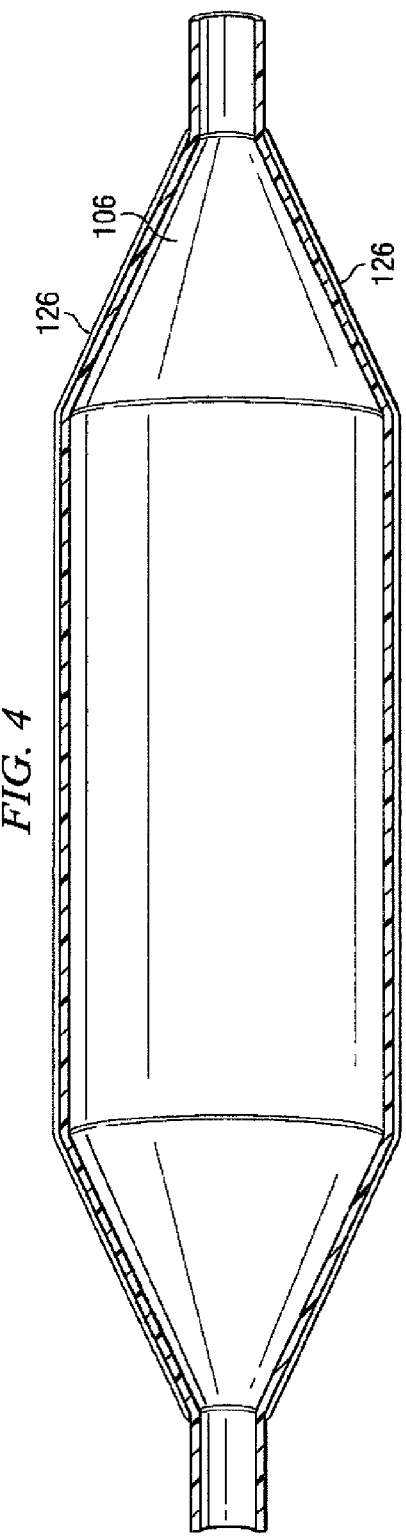
FIG. 4 illustrates a balloon base layer having an adhesive layer.

With reference to FIG. 4, integral layers of the fiber-reinforced balloon 10 are shown. In accordance a disclosed embodiment, a thin coating of an adhesive 126 is applied to the inflated polymer balloon base layer 100 or to the polymer-coated mandrel 122 prior to applying the first layer inelastic fibers 12. The adhesive 126 binds the fibers 13 sufficiently to hold them in position when the fibers 13 are placed on the base layer balloon 100. In accordance with one embodiment, a very thin coat of 3M-75 adhesive 126 is applied to the base layer balloon 100. 3M-75 is a tacky adhesive available from the 3M Company, Minneapolis, Minn.

Figure 5:
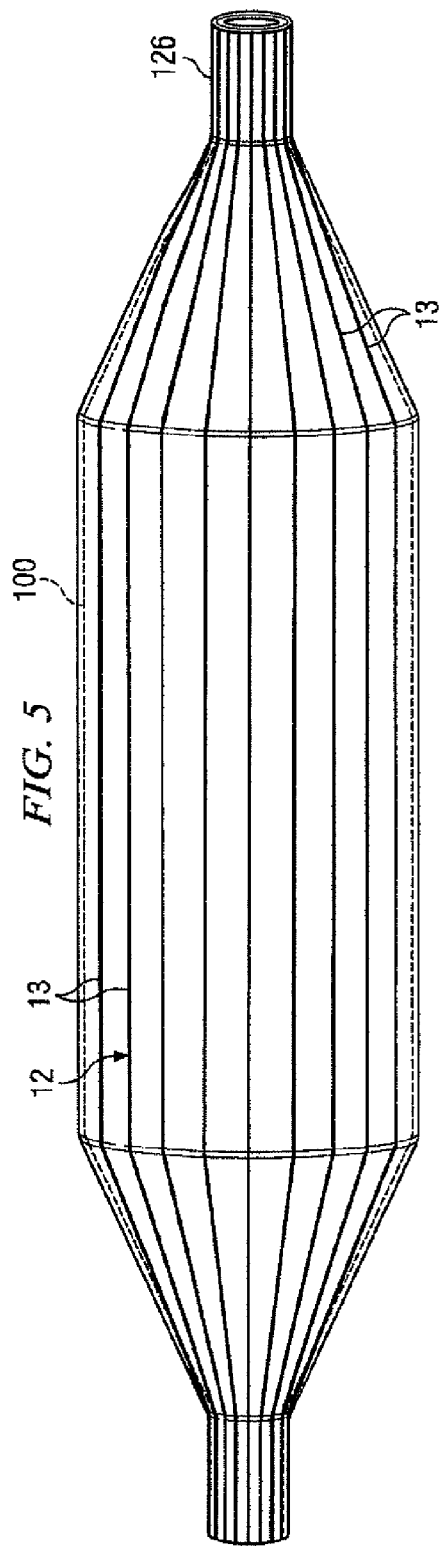
FIG. 5 illustrates a first fiber layer.

With reference to FIG. 5, integral layers of the fiber-reinforced balloon 10 are shown. One or more fibers 13 are applied to the polymeric base layer 100 to form a first fiber layer 12. The first fiber layer 12 may be referred to as the "primary wind."

The fibers 13 of the first fiber layer 12 may be inelastic fiber, typically made of an inelastic fibrous material. An inelastic fiber is a fiber that has very minimal elasticity or stretch over a given range of pressures. Some fibrous materials are generally classified as inelastic although the all fibrous material may have a detectable, but minimal, elasticity or stretch at a given pressure.

The fibers 13 of the first fiber layer 12 may be high-strength fibers, typically made of a high-strength fibrous material. Some high strength inelastic fibrous materials may include Kevlar, Vectran, Spectra, Dacron, Dyneema, Terlon (PBT), Zylon (PBO), Polyimide (PIM), other ultra high molecular weight polyethylene, aramids, and the like.

In a disclosed embodiment, the fibers 13 of the first fiber layer 12 are ribbon-shaped, where the width of the fiber is larger than the thickness of the fiber. The fibers 13 may be flat so that the fiber has a rectangular cross-section. The fibers 13 used in the initial layer of fibers 12 may all be fibers 13 made of the same material and the same shape. Fibers 13 made from different materials may be used in the initial fiber layer 12. Fibers 13 made in different shapes may be used in the initial fiber layer 12.

Ultra High Molecular Weight Polyethylene fiber 13, which has been flattened on a roll mill may be used to form the first fiber layer 12. To the flattened fiber 13 is applied a thin coat of a solution of polyurethane adhesive in a 60-40 solution of methylene chloride and methylethylketone. The fibers 13 may be arranged as 30 longitudinal fibers, each substantially equal in length to the length 118 of the long axis of the balloon 100.

The fibers 13 of the initial fiber layer 12, in accordance with the disclosed embodiment, are arranged so that each fiber 13 is substantially parallel to the long axis of the balloon 100. Longitudinally placed fibers 13 are fibers 13 placed along the long axis of the balloon 100. The fibers 13 may be parallel to each other. The density of the fibers 13 in the initial fiber layer 12 is determined by the number of fibers 13 or fiber winds per inch and the thickness of the fibers 13.

In a disclosed embodiment of the first fiber layer 12 having longitudinally-placed fibers 13, a fiber density of generally about 15 to 30 fibers 13 having a fiber thickness of about 0.0005 to 0.001 inch and placed equidistant from one another provide adequate strength for a standard-sized fiber-reinforced medical balloon 10. Kevlar® fibers 13 may be positioned along the length of the balloon 100 to form the first fiber layer 12. Each of the fibers 13 is substantially equal in length to the length 118 of the long axis of the balloon 100. Twenty-four fibers 13 may be positioned substantially equally spaced from each other.

The fiber 13 used for the primary wind may have a thickness of 0.0006 inch. Fiber 13 with a thickness of 0.0005 inch may be used instead. The resulting composite balloon 10 is axially and radially non-compliant at very high working pressures. The fiber-reinforced balloon 10 has very high tensile strength and abrasion and puncture resistance. High strength ultra-high molecular weight polyethylene fiber may be used.

The first fiber layer 12 may prevent longitudinal extension of the completed fiber-reinforced balloon 10. The longitudinally placed fibers 13 may be parallel to or substantially parallel to the long axis of the base layer balloon 100 for maximum longitudinal stability of the fiber-reinforced balloon 10.

Figure 6:
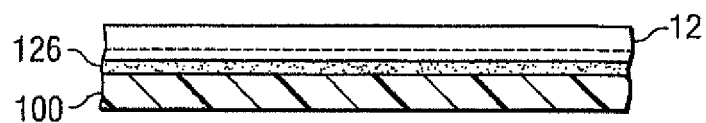
FIG. 6 illustrates a cross-section of a balloon base layer, adhesive layer and first fiber layer.

With reference to FIG. 6, a cross-section of the integral layers of a fiber-reinforced balloon 10 is depicted. A base layer 100 is coated with an adhesive layer 126. The first fiber layer 12 is positioned on the base layer 100, held at least partially in place by the adhesive layer 126.

Figure 7:
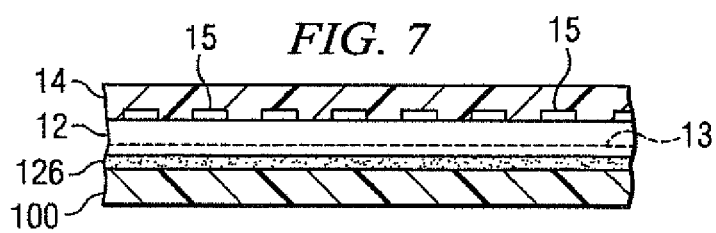
FIG. 7 illustrates a cross-section of a balloon base layer, adhesive layer and first fiber layer.

In accordance with a disclosed embodiment, a second fiber layer 14 made with one or more high-strength inelastic fibers 15 is positioned along circumference of the balloon 100, as shown in FIG. 7. The circumferentially placed fibers 15 may be transverse or substantially transverse to the long axis of the balloon 100. The circumferential fibers 15 may prevent or minimize distension of the balloon diameter 116 at pressures between the minimal inflation pressure and the balloon burst pressure.

The fibers 15 of the second fiber layer 14 may be inelastic fiber, typically made of an inelastic fibrous material. An inelastic fiber is a member of a group of fibers that have very minimal elasticity or stretch in a given range of pressures. Some fibrous materials are generally classified as inelastic although the all fibrous material may have a detectable, but minimal elasticity or stretch at a given pressure.

The fibers 15 of the second fiber layer 14 may be high-strength fibers, typically made of a high-strength fibrous material. Some high strength inelastic fibrous materials may include Kevlar, Vectran, Spectra, Dacron, Dyneema, Terlon (PBT), Zylon (PBO), Polyimide (PIM), other ultra high molecular weight polyethylene, aramids, and the like.

In a disclosed embodiment, the fibers 15 of the second fiber layer 14 are ribbon-shaped, where the width of the fiber is larger than the thickness of the fiber. The fibers 15 may be flat so that the fiber has a rectangular cross-section. The fibers 15 used in the second layer of fibers 14 may all be fibers 15 made of the same material and the same shape. Fibers 15 made from different materials may be used in the second fiber layer 14. Fibers 15 made in different shapes may be used in the second fiber layer 14.

Ultra High Molecular Weight Polyethylene fiber 15, which has been flattened on a roll mill may be used to form the second fiber layer 14. To the flattened fiber 15 is applied a thin coat of a solution of polyurethene adhesive in a 60-40 solution of methylene chloride and methylethylketone. The fibers 15 may be arranged as a second fiber layer 14 may have a fiber density of 54 wraps per inch. The fibers 15 may be coated with the adhesive solution to form the outer coating layer 16.

The fibers 15 of the second fiber layer 14 may be perpendicular to or substantially perpendicular to the fibers 13 placed longitudinally to form the first fiber layer 12. This transverse placement of the first fiber layer 12 and the second fiber layer 14 allows for maximum radial stability of the fiber-reinforced balloon 10. The placement of the fiber layers 12 and 14 distributes the force on the balloon surface equally, creating pixelized pressure points of generally equal shape, size and density.

The fibers 13 of the first fiber layer 12 may be the same as or different from the fiber 15 of the second fiber layer 14. Specifically, the fibers 15 of the second fiber layer 14 may be made of a different material or materials than the fibers 13 of the first layer 12. The fibers 15 of the second layer 14 may be shaped differently from the fibers 13 of the first fiber layer 12. The characteristics of the fibers or combination of fibers used for the first or second fiber layers may be determined from the specific properties required from the resulting fiber-reinforced balloon 10.

With respect to the fiber density of the second fiber layer 14, in accordance with the disclosed embodiment, fiber 15 having a thickness of about 0.0005 to 0.001 inch and arranged in parallel lines with about 50 to 80 wraps per inch provides generally adequate strength. A single fiber 15 may preferably form the second fiber layer 14, with the fiber 15 wound in a generally parallel series of circumferential continuous loops.

For a standard-sized medical balloon 10, the single fiber 15 may be about 75-100 inches long. Kevlar® fiber 15 may be applied radially around the circumference of and over substantially the entire length 118 of the long axis of the balloon 100. The fiber 15 has a thickness of 0.0006 inch and is applied at a wind density of 60 wraps per inch.

Figure 8:
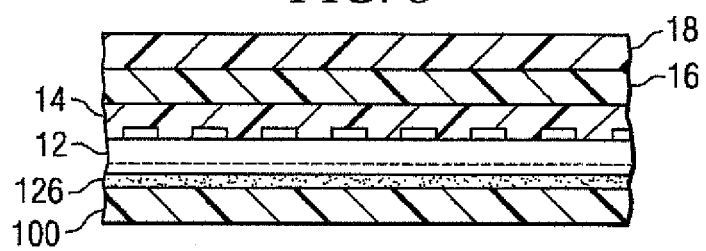
FIG. 8 illustrates a cross-section of a balloon base layer, an adhesive layer, a first fiber layer, a second fiber layer, an outer coating layer and a final layer.

With reference to FIG. 8, a cross section of the integral layers of a fiber-reinforced medical balloon 10 is shown. The first fiber layer 12 and the second fiber layer 14 may be coated with an outer coating layer 16. The outer coating layer 16 may be, in the disclosed embodiment, a polymeric solution. The outer coating layer 16 may be a cured polymeric solution. A fiber-wound based PET balloon 10 may be coated with a 10% solution of 5265 polyurethane in dimethylacetamide (DMA) that has been allowed to cure at room temperature. Five additional coatings of the polurethane solution may be used to form the outer coating layer 16. The resulting composite fiber-reinforced balloon 10 is non-compliant and exhibits superior burst strength and abrasion and puncture resistance. One or more additional protective layers 18 may be positioned on the outer coating layer 16, to provide additional layers of protection.

A composite structure typically including balloon base layer 100, an adhesive 126, a first fiber layer 12, a second fiber layer 14 and an outer coating layer 16 forms a composite, non-compliant fiber-reinforced balloon 10 particularly suitable for medical uses. The outer coating layer 16 of the fiber/polymeric matrix secures and bonds the fibers 13 and 15 to the underlying PET balloon base layer 100. Typically, the relative movement of the fibers 13 and 15 are fixed when the fiber-reinforced balloon 10 is initially deflated, and then subsequently inflated and deflated during use.

A wax mandrel 122 may be coated with a very thin layer (0.0002 inch) of polyurethane to form a balloon base layer 100. After the polyurethane has been cured, adhesive 126 and fibers may be applied to form a first fiber layer 12 and a second fiber layer 14. Several coats of polyurethane may be applied to form the outer coating layer 16. The wax mandrel 122 is then exhausted by dissolving in hot water to form a non-compliant, very high strength, abrasion-resistant, composite fiber-reinforced balloon 10.

A balloon-shaped solid mandrel 122 made of a low melting temperature metal alloy may be coated with a thin layer of polyurethene/DMA solution (10%) as an base layer 100. Fibers may be positioned to form a first fiber layer 12 and a second fiber layer 14. The fibers 13 and 15 may be coated with a polyurethene/DMA outer coating layer 16.

A mandrel 122 may be coated with a very thin layer of PIM Polyimide (2,2-dimethylbenzidine) in solution in cyclopentanone as a base layer 100. Polyimide fibers may be positioned to form a first fiber layer 12 and the second fiber layer 14. The composite balloon 10 may have an outer coating layer 16 of the PIM solution. When the mandrel 122 is removed, the fiber-reinforced balloon 10 is characterized by a high strength and puncture resistance. The balloon 10 will be formed with an extremely cohesive fiber/matrix composite wall that is resistant to delamination.

Figure 9:
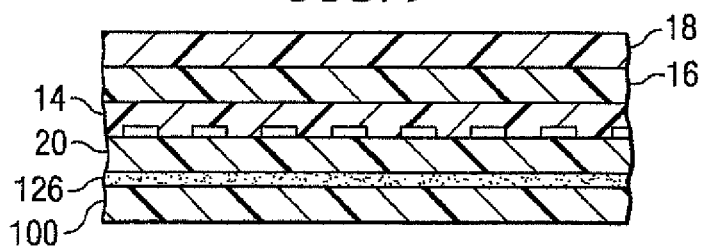
FIG. 9 illustrates a cross-section of a balloon base layer, an adhesive layer, a first fiber layer, a second fiber layer and an outer coating layer.

With reference to FIG. 9, a cross-section of the integral layers of a fiber-reinforced balloon 10 in accordance with one embodiment is shown. The longitudinal first fiber layer 12 may be replaced by a longitudinally oriented thin film 20 made of Polyimide film. The film 20 may be cut into a balloon-shaped pattern and applied to the mandrel 122, over which the Polyimide hoop fibers 14 and the PIM solution 16 may be applied.

The thickness of the polymeric outer coating layer 16 may be determined by the characteristics of the desired fiber-reinforced balloon 10. The polymeric solution used for the outer coating layer 16 may be made of the same polymer as the polymer base balloon layer 100. The outer coating layer 16 may be made from a different polymer than the inflated polymeric balloon base layer 100. Where the polymers are different, the polymers may be chosen to be compatible to reduce or prevent separation of the composite balloon 10.

Polymers and copolymers that may be used as the outer coating layer 16 of the fiber/polymeric matrix include the conventional polymers and copolymers used in medical balloon construction. Typical suitable substances may include polyethylene, nylons, polyethylene terephthalate (PET), polycaprolactam, polyesters, polyethers, polyamides, polyurethanes, polyimides, ABS copolymers, polyester/polyether block copolymers, ionomer resins, liquid crystal polymers, and rigid rod polymers.

A final layer 18, generally a homogeneous polymeric or other material layer, may be positioned on the outer layer 16 as a protective layer. The final laminate 18 may be applied as a film, a spray coating, by dipping or other deposition process. The resulting final laminate 18 is rendered more resistant to damage of the fibers. The final composite improves resistance to abrasion. The added layer 18 provides improved stent retention for deployment. The polymeric final layer 18 lowers the final durometer of the balloon surface.

While the fiber reinforced balloon 10 having a balloon base layer 100, a first fiber layer 12 and second fiber layer 14 and an outer coating layer 16 forms the balloon 10 of the disclosed embodiment, it will be recognized by those skilled in the art that other variations of the embodiment may be formed. In particular, a variety of combinations of fiber layers, fiber layer orientations and fabrics may be used to form various medical balloons having various attributes.

With reference to FIG. 10, a fiber reinforced balloon 10 in accordance with the disclosed embodiment, is shown. In this embodiment, the fibers 13 of the first fiber layer 12 lie parallel to the long axis of the balloon 10.

With reference to FIG. 11, a fiber reinforced balloon 45, in accordance with another embodiment is shown. The fiber-reinforced balloon 45 may include a first fiber layer 46 with fibers 47 that lie at an angle to the longitudinal axis of the balloon 45. In this embodiment, neither the fibers 47 of the first fiber layer 46 nor the fibers 49 of the second fiber layer 48 are positioned parallel to the longitudinal axis of the balloon 45. In accordance with one embodiment, the fibers 47 of the first fiber layer 46 may be positioned parallel to a line at a five degree angle to a line parallel to the longitudinal axis of the balloon base layer 100. In accordance with another embodiment, the fibers 47 of the first fiber layer 46 may be positioned parallel to a line at a twenty degree angle to a line parallel to the longitudinal axis of the balloon base layer 100.

In accordance with another embodiment, the fibers 47 of the first fiber layer 46 may be positioned parallel to a line at a thirty degree angle to a line parallel to the longitudinal axis of the balloon base layer 100. In accordance with another embodiment, the fibers 47 of the first fiber layer 46 may be positioned parallel to a line at a forty-five degree angle to a line parallel to the longitudinal axis of the balloon base layer 100. It will be apparent to those having skill in the art that the fibers 47 may be placed at any appropriate angle.

In accordance with the disclosed embodiment, the fibers 15 of the second fiber layer 14 lie parallel to the circumference of the balloon 10. With reference to FIG. 12, a fiber-reinforced balloon 40 in accordance with another embodiment is shown. The fiber reinforced balloon 40 may include a second fiber layer 43 with fibers 44 that lie at an angle to the circumference of the balloon 40. In accordance with one embodiment, the fibers 44 of the second fiber layer 43 may be positioned parallel to a line at a five degree angle to a line parallel to the circumference of the base balloon 100.

In accordance with one embodiment, the fiber 44 of the second fiber layer 43 may be positioned parallel to a line at a twenty degree angle to a line parallel to the circumference of the base balloon 100. In accordance with one embodiment, the fiber 44 of the second fiber layer 43 may be positioned parallel to a line at a thirty degree angle to a line parallel to the circumference of the base balloon 100. In accordance with one embodiment, the fiber 44 of the second fiber layer 43 may be positioned parallel to a line at a forty-five degree angle to a line parallel to the circumference of the base balloon 100. It will be apparent to those skilled in the art that the fibers 44 may be placed at any appropriate angle.

In accordance with the disclosed embodiment, the fibers 42 of the first fiber layer 41 and the fibers 44 of the second fiber layer 43 are positioned perpendicularly relative to each other. With reference to FIG. 13, a fiber-reinforced balloon 50 in accordance with another embodiment is shown. A fiber-reinforced balloon 50 may include fibers 52 of the first fiber layer 51 and fibers 54 of the second fiber layer 53 positioned relatively at an angle other than a right angle.

With reference to FIG. 14, a fiber-reinforced balloon 55 in accordance with one embodiment is shown. It will be apparent to those having skill in the art that the fibers 57 of the first fiber layer 56 and the fiber 59 of the second fiber layer 58 may be positioned at any appropriate angle. Placing the fiber 57 of the first fiber layer 56 and the fibers 59 of the second fiber layer 58 parallel to each other will result in a balloon 55 with less strength than a balloon 55 where the fibers 57 and 59 are positioned relatively at an angle.

With reference to FIG. 15, a fiber-reinforced balloon 60 in accordance with another embodiment is shown. The fiber-reinforced balloon 60 may include a third fiber layer 63 may be positioned atop the second fiber layer 62. Typically, the fibers 66 of the third fiber layer 63 may form an angle with the fibers 64 of the second fiber layer 62 and the fibers 67 of the first fiber layer 61. The fibers 66 of the third fiber layer 63 may be formed of the same material as the fibers 64 of the second fiber layer 62 or the fiber 67 of the first fiber layer 61 or both.

The fibers 66 of the third fiber layer 63 may be formed in the same shape as the fibers 64 of the second fiber layer 62 or the fibers 67 of the first fiber layer 61 or both. An adhesive 126 may be used to secure the placement of the fibers 66 of the third fiber layer 63 on the fibers 64 of the second fiber layer 62.

In one embodiment, the fibers 64 of the second fiber layer 62 may be positioned at a small acute angle, typically about 10 degrees to the longitudinal fibers 67 of the first fiber layer 61. A third fiber layer 63 having a fiber 66 at an opposite angle relative to the longitudinal fibers 67 of the first fiber layer 61 may help minimizing radial distension. FIG. 16 depicts a fiber-reinforced balloon 60 having a first fiber layer 61, a second fiber layer 62 and a third fiber layer 63.

Figure 17B:
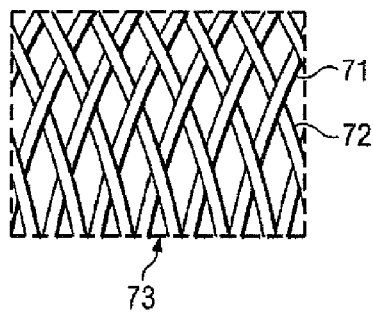
FIG. 17B is an enlarged illustration of a portion of the balloon of FIG. 17A.

With reference to FIG. 17, a fiber-reinforced balloon 70 having a woven fiber layer 73 in accordance with one embodiment is shown. Medical textile products are based on fabrics, of which there are four types: woven, knitted, braided, and non-woven. Weave patterns are typically comprised of two thread systems, designated wasp and weft. Warp threads 72 run along the length of the fabric, circumferentially when the fabric is applied to a balloon 70. Weft threads 71 run along the width. It should be noted that these designations are arbitrary and the direction of the warp and weft threads may not correspond to the axis or circumference of a balloon. In the process of weaving, threads are interlaced in different ways to form various weave patterns. It will be recognized that fiber-reinforced balloon 70 could be made using any suitable fabric, whether woven, knitted, braided or non-woven.

The threads of the fabric may be formed from a variety of substances, typically polymers. In selecting a polymer, it should be recognized that suitable polymer chains may be linear, long, and flexible. The side groups should be simple, small, or polar. Suitable polymers may be dissolvable or meltable for extrusion. Chains should be capable of being oriented and crystallized.

Common fiber-forming polymers include cellulosics (linen, cotton, rayon, acetate), proteins (wool, silk), polyamides, polyester (PET), olefins, vinyls, acrylics, polytetrafluoroethylene (PTFE), polyphenylene sulfide (PPS), aramids (Kevlar, Nomex), and polyurethanes (Lycra, Pellethane, Biomer). Each of these materials is unique in chemical structure and potential properties.

The woven fiber layer 73 typically covers the entire length and circumference of the barrel of the balloon 70. To form a restraining structure integral to the fiber-reinforced balloon 70, weft fibers 71 and warp fibers 72 may be woven by passing a weft fiber 71 over and then under the warp fibers 72 across the surface of the balloon 70. The woven weft fibers 71 and warp fibers 72 may form a woven fiber layer or other fabric layer 74. The woven fiber layer 74 may be used in place of either the first fiber layer 12 or the second fiber layer 14 as those layers are described in other embodiments.

A weft fiber 71 is typically woven with a warp fiber 72 in an interlocking fashion with each fiber passing over and then under the sequence of transverse fibers. It will be recognized by those skilled in the art that the weft fibers 71 may be woven in a variety of weave patterns with warp fibers 72. Pre-woven fabric may be applied as a woven fabric layer 74 to the balloon directly. An adhesive layer 126 may be used to fix the position of the fabric layer 74 on the base balloon layer 100.

Figure 18:
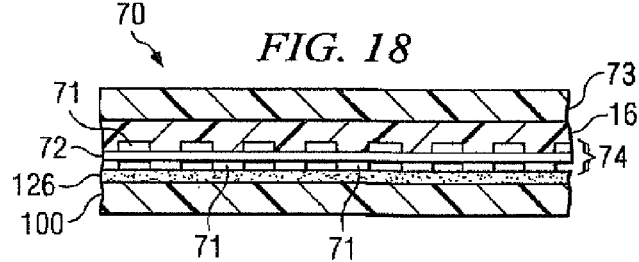
FIG. 18 illustrates a cross-section including a woven fiber layer.

With reference to FIG. 18, a cross-section of a fiber-reinforced balloon 70 including a woven fabric layer 74 is shown. In one embodiment, the woven fabric layer 74 may be coated with a polymer. In accordance with another embodiment, a fiber may be wound circumferentially as a second fiber layer 73 over the woven fiber layer 74. The woven fiber layer 74 and circumferential fiber layer 73 may be coated with an outer coating layer polymer 16. The angles formed between the woven fibers 71 and 72 remain substantially unchanged between the inflated state of the balloon 70 and the deflated state of the balloon 70. The balloon 70 is typically folded when deflated, maintaining the angles between the fibers 71 and 72 upon deflation.

Figure 19:
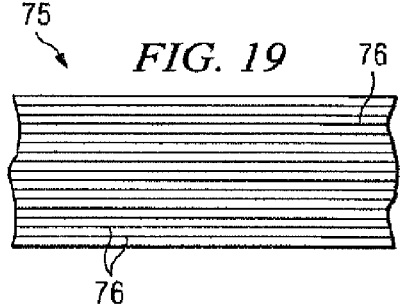
FIG. 19 illustrates a fabric layer including taut parallel fibers.
Figure 20:
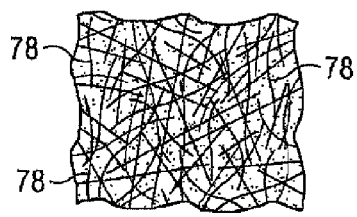
FIG. 20 illustrates a fabric layer including matted fibers.

With reference to FIGS. 19 and 20, non-woven fabrics are shown. In accordance with one embodiment, non-woven fabric may be used to form a non-woven fabric layer 75. The non-woven fabric layer 75 may be positioned directly on the base balloon layer 100. An adhesive layer 126 may be used to fix the position of the non-woven fabric layer 75 to the base balloon layer 100.

The non-woven fabric layer 75 may be formed from parallel taut fibers 76 joined with a binding solution such as a polymeric solution. The non-woven fabric layer 75 may be cut into a pattern that may allow the applied fabric layer 75 to cover the base balloon 100 or mandrel 122.

In accordance with another embodiment, the non-woven fabric layer 77 may be formed as matted fibers 78. The matted fibers 78 may be joined with a binding solution such as a polymeric solution. Typically the angles between the fibers 78 of the matted fiber layer 77 are randomly assorted. When the binding solution has been applied to the matted fibers 78, the angles between the fibers 78 does not substantially change, regardless of the pressures applied to the surface of the matted fabric layer 77.

The non-woven fiber layer 75 may be used in place of either the first fiber layer 12 or the second fiber layer 14. The non-woven fiber layer 75 may be applied from pulp, chopped or other forms of individual fiber elements. The matted fiber 77 may be applied by spraying, dipping, co-extrusion onto a carrier, wrapping a pre-formed mat or any other suitable technique.

In one embodiment, the non-woven fabric layer 75 may be coated with a polymer. In accordance with another embodiment, a fiber 15 may be wound circumferentially over the non-woven fiber layer 75 to form a second fiber layer 14. The non-woven fiber layer 75 and circumferential fiber layer 14 may be coated with a polymer outer coating layer 16.

The fiber-reinforced balloon 10, as described, may be substantially non-compliant. That is, the balloon 10 may be characterized by minimal axial stretch and minimal radial distention and by the ability not to expand beyond a predetermined size on pressure and to maintain substantially a fixed profile.

Figure 21:
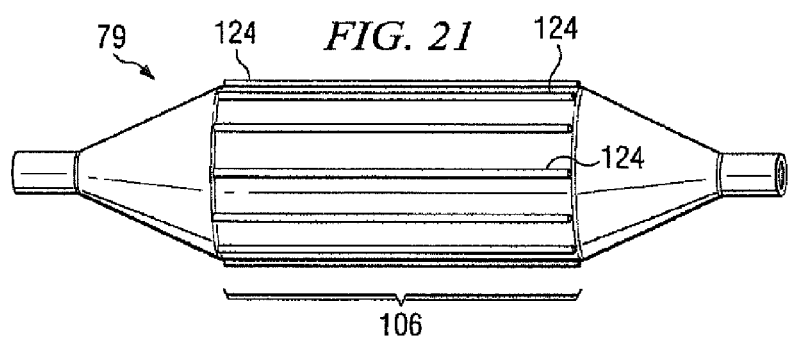
FIG. 21 illustrates a medical balloon having attached strengthening rods.

With reference to FIG. 21, strengthening rods 124 may be placed around the circumference of a balloon 100. Strengthening rods 124 provide pressure points on the exterior surface of the inflated balloon, focusing the inflation pressure on the line formed by the outermost surface of the strengthening rods 124.

In accordance with the disclosed embodiment, the strengthening rods 124 are positioned longitudinally around the circumference of the balloon 100. The strengthening rods 124 may be made from PEEK (polyetheretherketone) or any other suitable material. The strengthening rods 124 may be used on a fiber-reinforced balloon, or any other polymeric or medical balloon 79.

The strengthening rods 124 may be of any appropriate size, such as the length 106 of the barrel of the balloon 79. The strengthening rods 124 may have any appropriate cross-sectional geometry, including a circular cross-section, a square cross-section, a triangular cross-section, a hexagonal cross-section or any other appropriate shape. In another embodiment, the strengthening rods 124 could be fashioned to form an outward blade surface. The diameter of the strengthening rods 124 must be small enough to permit the catheter to be effectively used. The number of strengthening rods and the diameter of the strengthening rods 124 will be limited by the cross-sectional diameter of the deflated medical balloon including the strengthening rods 124.

Figure 22:
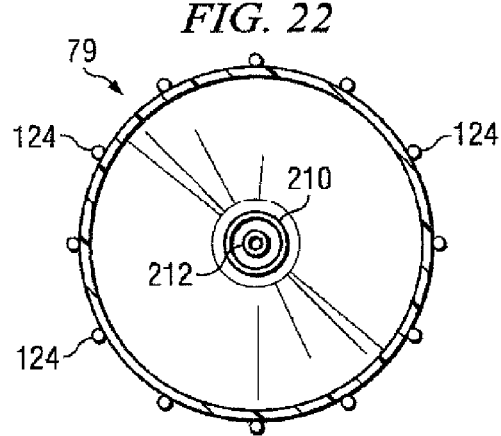
FIG. 22 illustrates a cross-section of a medical balloon having attached strengthening rods.

With reference to FIG. 22, a cross-section of a balloon 79 with strengthening rods 124 is shown. The strengthening rods 124 may be placed in any suitable position relative to the longitudinal axis of the balloon 79. The strengthening rods 124 may be of any suitable length. In accordance with the disclosed embodiment, the strengthening rods 124 are positioned substantially parallel to the long axis of the balloon 79, with a length 106 and position along to the working distance of the barrel of a balloon 79. A cross-section of the outer tube 210 and the inner tube 212 of the catheter 200 is shown.

The strengthening rods 124 may be secured to the balloon 79 with a homogeneous outer polymeric layer 16. The homogeneous outer layer 16 may have been applied as a film, spray coating, dipping or other suitable processes.

When used in angioplasty, the strengthening rods 124 cause the force generated by the pressure of the inflated balloon 79 to be concentrated at the strengthening rod 124 outer surface, thus providing improved fracturing and movement of the calcifications, lesions or other causes of stenosis inside the affected vessel. When used in stent deployment, the force required to deploy the stent is concentrated at the outer surface of the strengthening rods 124, protecting the balloon surface 79 from abrasion or puncture.

Figure 23:
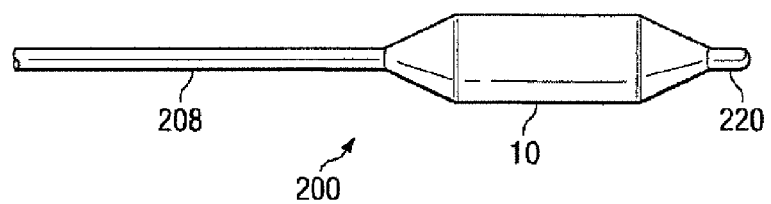
FIG. 23 illustrates a balloon catheter.

With reference to FIG. 23, a fiber-reinforced balloon catheter 200 is shown. A fiber-reinforced medical balloon 10 may typically be fixed near the distal end 220 of a catheter tube 208. Balloon catheters 200 having inflatable balloon attachments have commonly been used for reaching internal regions of the body for medical treatments, such as in coronary angioplasty and the like. The fiber-reinforced medical balloon 10 may be exposed to relatively large amounts of pressure during these procedures. The profile of the deflated balloon 10 must be relatively small in order to be introduced into blood vessels and other small areas of the body.

Figure 24:
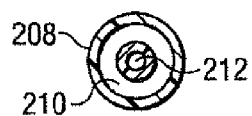
FIG. 24 illustrates a cross-section of a balloon catheter tube.

With reference to FIG. 24, a cross-section of a coaxial catheter tube is shown. A dilating catheter assembly 200 may include a coaxial tube catheter tube 208, including an outer channel 210 and an inner channel 212. The coaxial catheter tube 208 may be adapted to be inserted into the patient and attached to a connector structure 230 which enables both the inner 212 and outer channels 210 of the coaxial catheter 200 to be supplied with medium such as radio-contrast fluid.

Figure 25:
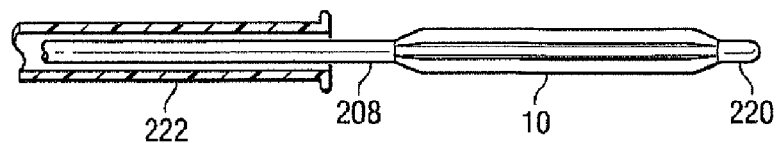
FIG. 25 illustrates a deflated fiber-reinforced medical balloon.

With reference to FIG. 25, a deflated fiber-reinforced balloon 10 is shown. Catheter 200 assembly has an inner channel 212 and an outer channel 210 which extend the length of the catheter tube 208. The distal end 220 of the outer tube 210 may be connected to a fiber-reinforced balloon 10. A folding sheath 222 may be provided for mechanical deflation of the fiber-reinforced balloon 10.

With reference to FIG. 26, A coupling device 230, such as a conventional syringe luer, may be used to couple the catheter tube 208 to a syringe 214 used to inflate the fiber-reinforced balloon 10. The flange portion 232 of the coupling device 230 may be adapted to screw into a coupling portion 216 of the syringe 212, forming a seal. The wing portions 234 of the coupling device 230 may be used to twist the flange portion 232 into the coupling portion 216 of the syringe 214. The coupling body 236 of the coupling device 230 allows the medium, typically a liquid such as a radio-contrast solution to pass from the syringe 214 to the fiber-reinforced balloon 10.

Figure 27:
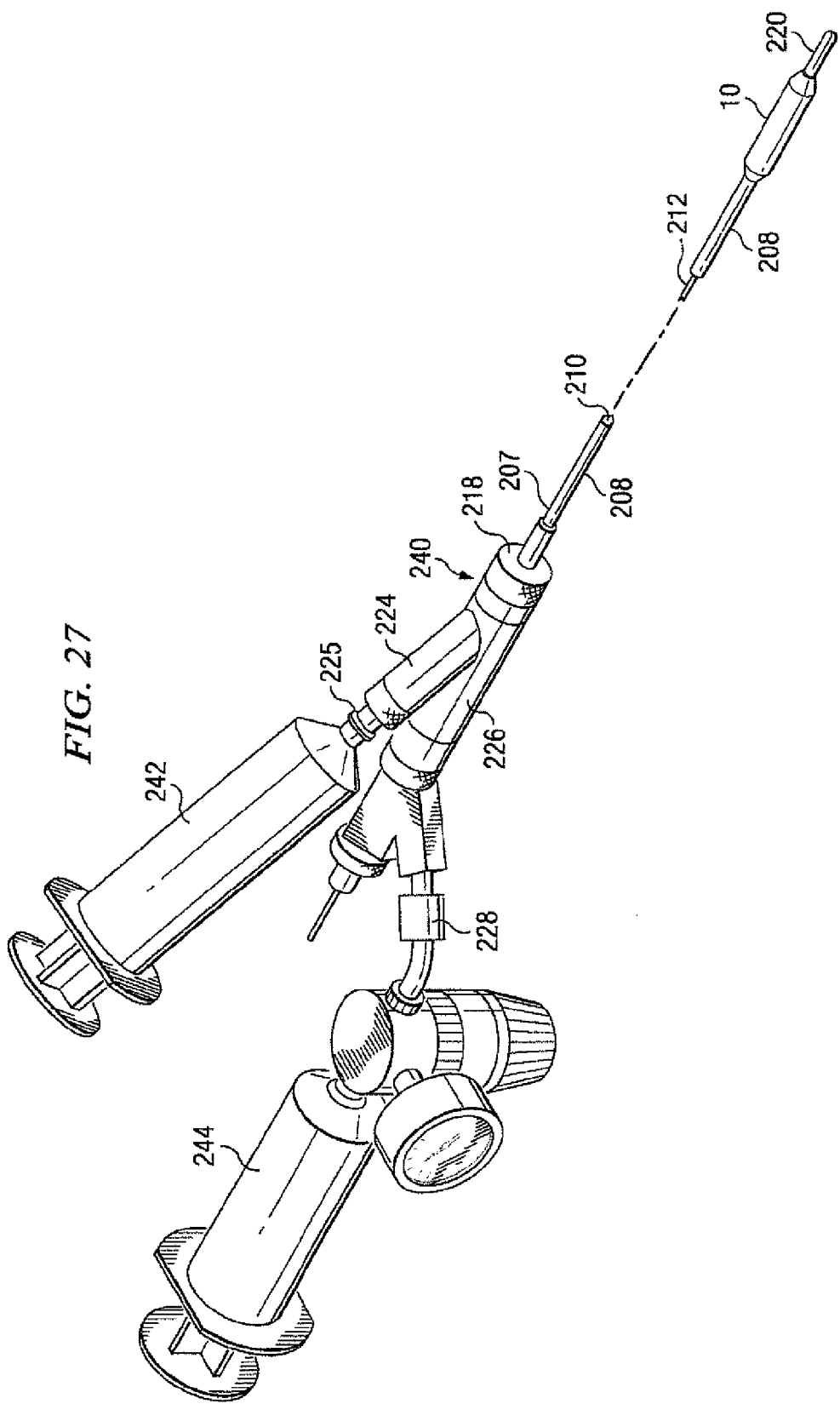
FIG. 27 illustrates a balloon catheter and a pressurized fluid delivery system.

With reference to FIG. 27, a typical coaxial coupling device 240 with integral syringes 242 and 244 is shown. In accordance with one embodiment, the proximal end 207 of the catheter tube 208 including the coaxial channels 210 and 212 are fed into a connector assembly 218. The inner channel 212 may be fed into a side arm 224 where it is sealed into a fitting 225. The fitting 225 may be adapted to receive the front end of syringe 242.

A connecting arrangement 226 may connect the outer channel 210 into the main central arm of connector 240 which may be connected through a coupler assembly 227. The outer channel 210 may be fed into main arm 226 where it is sealed into a fitting 228. The fitting 228 may be adapted to receive the front end of a syringe 244.

With reference to FIG. 28, a blocked vessel 400, such as a blocked coronary artery, having vessel walls 402 and a vessel channel 406 is shown. The vessel 400 may be blocked by deposits 404 such as plaque. A fiber-reinforced balloon catheter 200 may be used to perform angioplasty as a treatment for a blocked artery 400. A fiber-reinforced balloon 10 may be used to open the heart artery 400 as an alternative to open heart surgery. The fiber-reinforced balloon catheter 200 for use in angioplasty typically includes a small, hollow, flexible tube 208 and a fiber reinforced balloon 10 attached near the end of the catheter tube 208.

A fiber-reinforced cutting balloon, formed with sharp aterotomes attached to the surface of the fiber reinforced balloon 10, may be used in some cases, particularly where the deposits 404 are solidified. A fiber-reinforced balloon 79 with strengthening rods 124 may be used in some procedures that may use a cutting balloon. In some cases, the strengthening rods 124 may be used to score the plaque 404, allowing the inflated fiber-reinforced balloon 10 to open the blockage 404 with less trauma than traditional balloon angioplasty.

The fiber-reinforced balloon 10 with strengthening rods 124 may be used for first-time interventions and for subsequent interventions. The fiber-reinforced balloon 10 with strengthening rods 124 may be particularly useful where the plaque 404 blockages are resistant lesions, particularly found in positions that are difficult or awkward to address. Bifurcation lesions, for example, occur at the Y-intersection of an artery 400. The inflation and deflation of the fiber-reinforced balloon 10 with strengthening rods 124 in this case helps open the blockage without allowing the plaque 404 to shift position. Fiber-reinforced balloons 10 with strengthening rods 124 may also be used in the treatment of restenosis. Lesions at the artery origins may also be effectively treated using a fiber-reinforced balloon 10 with strengthening rods 124.

Angioplasty typically starts with the patient lying on a padded table. Local pain medicine may be given. Catheters may be inserted in an artery, typically near the groin, in the femoral artery. The coronary arteries 400 may be remotely visualized by using X-rays and dye. These visualizations permit blockages in the heart vessels to be identified.

With reference to FIG. 29, a fiber-reinforced balloon catheter 200 is shown in an inflated state to open a blocked vessel 400. A fiber-reinforced balloon catheter 200 may be inserted into the vessel channel 406 or near the blockage 404 and inflated, thus widening or opening the blocked vessel 400 and restoring adequate blood flow to the heart muscle.

More specifically, the technique involves use of a fiber-reinforced catheter system 200 introduced via the femoral artery under local anesthesia. A pre-shaped guiding catheter may be positioned in the orifice of the coronary artery. Through this guiding catheter a second fiber-reinforced dilation catheter 200 is advanced into the branches of the coronary artery. The fiber-reinforced dilating catheter 200 has an elliptical-shaped distensible fiber-reinforced balloon portion 10 formed near the distal tip 220 of the catheter 200. The balloon portion 10 can be inflated and deflated. After traversing the stenotic lesion of the coronary artery 400, the distensible fiber-reinforced balloon portion 10 is inflated with fluid under substantial pressure which compresses the atherosclerotic material 404 in a direction generally perpendicular to the wall 402 of the vessel 400, thereby dilating the lumen of the vessel 400.

Balloon valvuloplasty, also known as valvuloplasty, balloon dilation or balloon mitral valvuloplasty, is a non-surgical procedure to open blocked heart valves that may use a fiber-reinforced balloon catheter 200.

The procedure involves the insertion of a fiber-reinforced balloon catheter 200 into the heart. An incision is made between the atria and the catheter 200 is moved into the blocked valve. When the balloon catheter 200 is in position, the fiber-reinforced balloon 10 may be inflated and deflated several times to open the valve. The non-compliance of the fiber-reinforced balloon 10 under pressure may provide benefits in such procedures.

Fiber-reinforced medical balloons 10 may be used in the treatment of broken or fractured vertebrae. A fiber-reinforced medical balloon 10 may be inserted into the region of the fracture. The minimally invasive procedure may require only a half-inch incision to insert the medical balloon 10. The fiber-reinforced balloon 10 may be inflated to an appropriate diameter to raise the collapsed bone. The space created by the fiber-reinforced balloon 10 may be filled with the a cementing substance, such as the cement used in hip and knee replacements.

Figure 30:
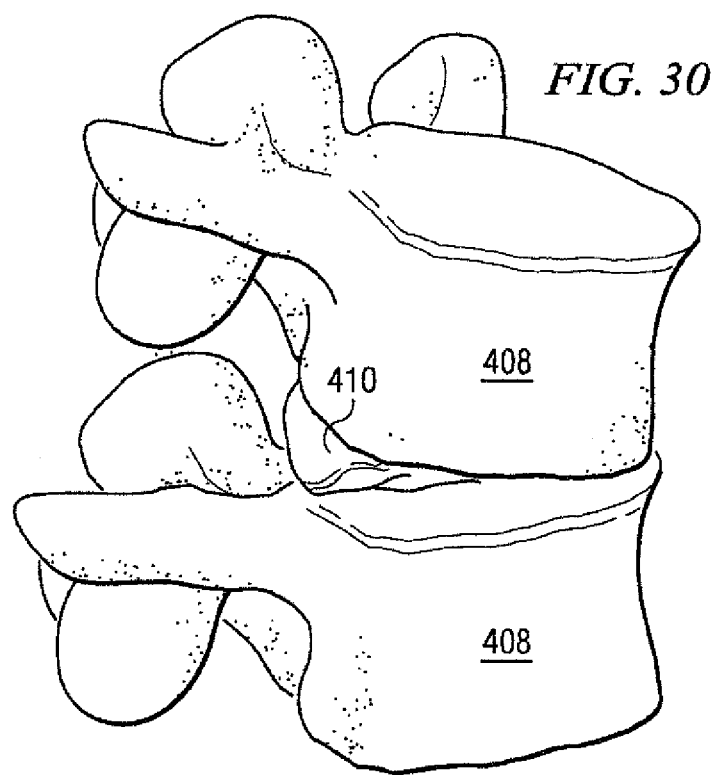
FIG. 30 illustrates vertebrae and a vertebral body.
Figure 31:
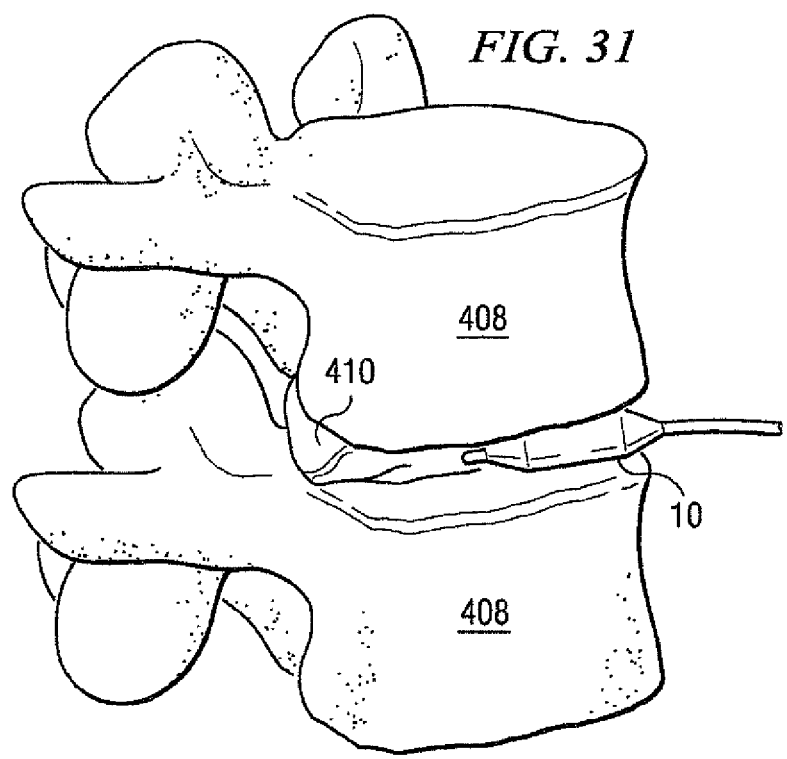
FIG. 31 illustrates vertebrae treated with a balloon catheter.

With reference to FIG. 30, a fiber-reinforced medical balloon 10 for a collapsed or ruptured disc is shown. The disk 410 between the vertebrae 408 may cease to separate the vertebrae 408 as shown. With reference to FIG. 31, a fiber-reinforced medical balloon 10 may be inserted between the vertebrae 408 and inflated. The space created by the fiber-reinforced balloon 10 may he filled with the a cementing substance, such as the cement used in hip and knee replacements.

Kyphoplasty may be used in the treatment of pain associated with osteoporotic compression fractures. The procedure helps stabilize the bone and restores vertebral body height. By inflating a fiber-reinforced medical balloon inside the fractured vertebra, the bone position is restored to allow for the injection of medical cement. This procedure stabilizes the fracture and promotes healing. The stabilization alone can provide immediate pain relief for many patients.

Kyphoplasty is performed through a small incision in the back. A narrow tube, placed in the incision, is guided to the correct position using fluoroscopy. The physician uses X-ray images to insert the fiber-reinforced medical balloon into the tube and into the vertebra. The fiber-reinforced balloon is gently inflated, elevating the fracture and returning the pieces of the vertebra to a more normal position. The inner bone is also compacted, creating a cavity which is filled with medical bone cement that hardens quickly and stabilizes the bone. Alternatively, the medical balloon may remain in the body and bone cement is filled inside the balloon to stabilize the vertebral body.

Another use of fiber-reinforced medical balloons is in carpal tunnel therapy. Balloon carpal tunnel-plasty may be performed using a fiber-reinforced balloon catheter device. The fiber-reinforced balloon catheter may be used with a specialized nerve protector to stretch and expand the transverse carpal ligament relieving the symptoms of carpal tunnel syndrome. The procedure may be performed through a one-centimeter size incision at the distal palmar crease ulnar to the palmaris longus in line with the fourth ray. The approach is identical to the single portal endoscopic technique. The fiber-reinforced medical balloon is used to dilate and expand the transverse carpal ligament to increase the spatial diameter of the carpal tunnel and relieve pressure on the median nerve alleviating symptoms of carpal tunnel syndrome.

Fiber-reinforced medical balloons may be used in radiation therapy. Where a tumor has been removed, a fiber-reinforced balloon catheter may be inserted. The inflated fiber-reinforced balloon fills the cavity where the tumor was removed from. Radiation is delivered into the fiber-reinforced balloon periodically.

Fiber reinforced medical balloons may be used in the treatment of nasolacrimal duct obstruction. Nasolacrimal duct obstruction can cause a condition called epiphora, characterized by chronic tearing. Dacryocystoplasty, a non-surgical treatment, is performed as an outpatient procedure after topical anesthesia, It entails the passage of a fluoroscopically guided wire through the lacrimal duct, followed by dilation of a fiber-reinforced balloon at the site of obstruction.

Another use of fiber-reinforced medical balloons is the treatment of benign prostatic hypertrophy. A fiber-reinforced balloon is inflated to dilate the prostatic urethra. Balloon urethroplasty is a therapeutic procedure intended to manage symptoms associated with benign prostatic hypertrophy. Under fluoroscopic guidance, a flexible catheter with a fiber-reinforced balloon attachment is placed in the urethra at the level of the prostate above the external sphincter. The fiber-reinforced balloon is then inflated for a short period of time to distend the prostatic urethra. This widening process is intended to relieve obstruction of the urethra caused by the enlarged prostate and to alleviate the symptoms of benign prostatic hypertrophy.

It will be appreciated by those skilled in the art having the benefit of this disclosure that this invention provides a non-complian medical balloon. It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

What is claimed is:

1. A non-compliant medical balloon, a wall of said balloon comprising:
    a base layer formed of a substantially inelastic polymer, said base layer including a cylindrical barrel section along a longitudinal axis and two conical end sections;
    a first fabric layer comprising a plurality of substantially inelastic fibers; and
    a second fabric layer comprising at least one substantially inelastic fiber.

2. The balloon of claim 1, farther including an adhesive layer for affixing at least one of the first and second fabric layers to the base layer.

3. The balloon of claim 1, wherein the first fabric layer spans substantially the entire outer surface of the barrel and conical end sections.

4. The balloon of claim 3, wherein the second fabric layer spans substantially the entire outer surface of the barrel and conical end sections.

5. The balloon of claim 1, further including an outer polymeric coating.

6. The balloon of claim 1, wherein the first fabric layer comprises a plurality of parallel fibers running substantially parallel to the longitudinal axis.

7. The balloon of claim 6, wherein the first fabric layer is in a cut pattern.

8. The balloon of claim 1, wherein at least one of the fibers is ribbon-shaped, having a width greater than the thickness of the fiber.

9. The balloon of claim 1, wherein the fibers of the first fabric layer form an angle with the at least one fiber of the second fabric layer.

10. The balloon of claim 1, wherein the fibers comprise a polymer from the following materials: cellulosic polymers, proteins, polyamides, polyester (PET), olefins, vinyls, acrylics, polytetrafluoroethylene (PTFE), polyphenylene sulfide (PPS), aramids, and polyurethanes.

11. The balloon of claim 1, wherein the second fabric layer comprises a plurality of inelastic fibers.

12. The balloon of claim 1, wherein the first or second fabric layer comprises a woven fabric layer.

13. non-compliant medical balloon, comprising:
    a base balloon formed of a substantially inelastic polymer, said base balloon including a cylindrical barrel section with a first diameter along a longitudinal axis, two conical sections adjoining the barrel section, and two cylindrical end sections, each with a second diameter smaller than the first diameter;
    a first non-woven fabric layer comprising a plurality of substantially inelastic first fibers, said first layer adhesively attached to the base balloon;
    a second non-woven fabric layer comprising at least one substantially inelastic second fiber; and
    an outer polymeric coating.

14. The balloon of claim 13, wherein the first fabric layer comprises a plurality of parallel fibers.

15. The balloon of claim 14, wherein the first fibers are parallel to the longitudinal axis of the balloon.

16. The balloon of claim 13, wherein. the first fibers comprise a polymer from the following materials; cellulosic polymers, proteins, polymides, polyester (PET), olefins, vinyls, acrylics, polytetrafluoroethylene, polyphenylene, sulfide (PPS), aramids, and polyurethanes.

17. The balloon of claim 13, wherein the second fabric layer further comprises a binding polymer.

18. A method of forming a non-compliant balloon comprising:
   providing, a base layer comprising, a substantially inelastic polymer;
   covering the base layer with a first non-woven fabric layer comprising a plurality of substantially inelastic first fibers;
   providing a second non-woven fabric layer comprising at least one second fiber; and
   coating the base layer and fabric layers with a polymeric coating.

19. The method of claim 18, wherein the covering step further comprises adhesively attaching the first fabric layer to the base layer.

20. The method of claim 18, wherein the step of providing a base layer comprises providing a base balloon comprising the substantially inelastic polymer.

21. The method of claim 18, wherein the step of providing a base layer comprises coating a mandrel with a substantially inelastic polymer and allowing the polymer to cure.

* * * * *

UNITED STATES PATENT AND TRADEMARK OFFICE
CERTIFICATE OF CORRECTION

| | | |
|---|---|---|
| PATENT NO. | : 8,961,849 B2 | Page 1 of 1 |
| APPLICATION NO. | : 13/690477 | |
| DATED | : February 24, 2015 | |
| INVENTOR(S) | : Hayes et al. | |

It is certified that error appears in the above-identified patent and that said Letters Patent is hereby corrected as shown below:

In The Claims

Column 16, line 18, please replace "farther" with -- further --.

Column 16, line 49, please insert -- A -- after 13.

Column 16, line 66, please delete "." after wherein.

Column 16, line 66, please delete "." after wherein.

Column 16, line 67, please replace ";" with -- : --.

Column 17, line 1, please replace "polymides" with -- polyamides --.

Column 17, line 2, please delete "," after polyphenylene.

Column 17, line 8, please delete "," after providing.

Column 17, line 8, please delete "," after comprising.

Signed and Sealed this
Twenty-sixth Day of January, 2016

Michelle K. Lee
*Director of the United States Patent and Trademark Office*